United States Patent
SaNogueira et al.

(10) Patent No.: US 8,163,272 B2
(45) Date of Patent: *Apr. 24, 2012

(54) SUNLESS TANNING SUBSTRATE

(75) Inventors: James SaNogueira, Suffern, NY (US); Olga V. Dueva-Koganov, White Plains, NY (US); Thomas Russo, Butler, NJ (US)

(73) Assignee: Playtex Products, Inc., Westport, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/479,566

(22) Filed: Jun. 30, 2006

(65) Prior Publication Data
US 2007/0020202 A1    Jan. 25, 2007

Related U.S. Application Data

(60) Provisional application No. 60/696,316, filed on Jul. 1, 2005.

(51) Int. Cl.
*A61K 8/00* (2006.01)
*A61K 8/18* (2006.01)
*A61Q 17/04* (2006.01)

(52) U.S. Cl. ............. 424/59; 424/60; 424/400; 424/401
(58) Field of Classification Search .................. 424/59, 424/60, 400, 401
See application file for complete search history.

(56) References Cited

U.S. PATENT DOCUMENTS

| | | | |
|---|---|---|---|
| 4,786,367 A | 11/1988 | Bogart et al. | |
| 4,891,227 A | 1/1990 | Thaman et al. | 424/443 |
| 4,891,228 A | 1/1990 | Thaman et al. | 424/443 |
| 5,211,883 A | 5/1993 | Yamashina et al. | |
| 5,645,822 A | 7/1997 | Meyer et al. | 424/59 |
| 5,750,092 A | 5/1998 | Meyer et al. | 424/59 |
| 6,428,799 B1 | 8/2002 | Cen et al. | 424/402 |
| 6,723,306 B2 * | 4/2004 | Gueret | 424/59 |
| 2001/0018527 A1 | 8/2001 | Razzano | |
| 2003/0224955 A1 | 12/2003 | Ribery | |
| 2004/0013617 A1 | 1/2004 | Rick | |
| 2004/0126342 A1 * | 7/2004 | Dicianna | 424/59 |
| 2005/0002978 A1 | 1/2005 | Crook et al. | 424/401 |
| 2005/0089486 A1 | 4/2005 | Spindler et al. | 424/59 |

FOREIGN PATENT DOCUMENTS

| | | |
|---|---|---|
| EP | 0547864 | 12/1992 |
| EP | 1 541 124 | 6/2005 |
| EP | 1 690 521 | 8/2006 |
| WO | WO 2007/005741 | 1/2007 |

OTHER PUBLICATIONS

Riedel, "Nonwoven Bonding Methods and Materials," Nonwoven World (1987), The Encyclopedia Americana, vol. 11, pp. 147-153 and vol. 26, pp. 566-581.
* International Search Report and Written Opinion dated Aug. 22, 2007 for International Application No. PCT/US06/25829.
Supplemental European Search Report dated Sep. 29, 2008 based on EP 06 79 9990.
Examination Report from Canadian Application No. 2,613,504 dated Jul. 7, 2011.

* cited by examiner

*Primary Examiner* — Johann Richter
*Assistant Examiner* — Luke Karpinski
(74) *Attorney, Agent, or Firm* — Ohlandt, Greeley, Ruggiero & Perle, L.L.P.

(57) ABSTRACT

The present invention provides a sunless tanning substrate having one or more sunless tanning enhancers, which adjust the rate of color development and/or adjust or customize the color developed on the skin. The present invention further provides a method of sunless tanning comprising the step of using the sunless tanning substrate of the present invention either prior to application, simultaneously with application, after application, or any combinations thereof, of one or more sunless tanning actives or agents to the skin. The present invention also provides a sunless tanning kit that includes one or more of the sunless tanning substrates.

25 Claims, 2 Drawing Sheets

SUNLESS TANNING SUBSTRATE

RELATED APPLICATION

This application claims the benefit of earlier filed pending Provisional Patent Application Ser. No. 60/696,316 filed on Jul. 1, 2005.

BACKGROUND OF THE INVENTION

1. Field of the Invention

The present invention relates to a sunless tanning substrate. More particularly, the present invention relates to a sunless tanning substrate that includes one or more components that provide fast development of a uniform, more intense, long-lasting and natural looking tan with more predictable, i.e., customized color characteristics, when applied to skin.

2. Description of the Related Art

U.S. Pat. Nos. 5,645,822 and 5,750,092 to Schering-Plough and European Patent Application No. 0 547 864 A1 describe attempts to provide sunless tanning. However, these and other approaches described in the art have certain drawbacks.

Products that are currently used for sunless tanning of the skin are based on the reaction of an active chemical present in the product with the skin's amino acids. Such chemicals are well known and include compounds having an aldehyde group, or compounds having a ketone group, such as, for example, dihydroacetone (DHA).

As an example, DHA gives skin a brownish color by reacting with the amino acids present in the sebum and stratum corneum by a known mechanism, namely the Maillard reaction.

Further, the distribution and nature of the amino acids is not uniform on the surface of the skin and as a result the intensity and shade of the color obtained may vary from one location to another on the treated skin, thereby causing the skin to have an uneven and/or unnatural look.

Further still, the duration of time required for development of skin color may be too long, which can lead to a decrease in the concentration of DHA on the surface of skin due to sweating or as a result of contact with clothing, thereby staining the clothing and resulting in an uneven color development on the skin.

It is very desirable to obtain a uniform and natural looking sunless tan over all skin surfaces that are treated with a sunless tanning composition that can develop color faster and last longer than formulations known in the art.

Thus, there is a need in the consumer products and cosmetic industry for a sunless tanning product that delivers increased tanning performance characteristics and eliminates the need for exposure to the damaging UV radiation from the sun for tanning. The present invention meets this need.

SUMMARY OF THE INVENTION

It is an object of the present invention to provide a sunless tanning substrate having one or more sunless tanning enhancers.

It is another object of the present invention to provide such a sunless tanning substrate that is in the form of a cloth, wipe, towel, towelette, sponge, foam, batting, puff, or any combinations thereof.

It is yet another object of the present invention to provide such a sunless tanning substrate having one or more sunless tanning enhancers that adjusts the rate of color development on the skin.

It is a further object of the present invention to provide such a sunless tanning substrate having one or more sunless tanning enhancers that adjusts and/or customizes the color developed on the skin.

It is still a further object of the present invention to provide a method of sunless tanning having the step of using the sunless tanning substrate with the one or more sunless tanning enhancers either prior to applying a sunless tanning active, simultaneous to applying a sunless tanning active, and/or after applying a sunless tanning active to the skin.

It is yet a further object of the present invention to provide a sunless tanning kit that includes a sunless tanning active composition and a sunless tanning substrate having one or more sunless tanning enhancers.

Accordingly, the present invention provides a sunless tanning substrate having one or more sunless tanning enhancers, which adjust the rate of color development and/or adjust or customize the color developed on the skin. The substrate may be used prior to application, simultaneously with application, after application, or any combinations thereof, of one or more sunless tanning actives or agents to the skin.

The present invention further provides a method of sunless tanning comprising the step of using the sunless tanning substrate of the present invention either prior to application, simultaneously with application, after application, or any combinations thereof, of one or more sunless tanning actives or agents to the skin. As a result of the method, the rate of color development and/or the color or color quality can be adjusted by the user.

The present invention also provides a sunless tanning kit. The kit includes a sunless tanning active or agent and a sunless tanning substrate having one or more sunless tanning enhancers. The kit allows a user to control or adjust the rate of color development on the skin and/or the color or color quality developed on the skin.

These and other objects and advantages of the present invention are achieved by the use of the sunless tanning compositions and method of sunless tanning according to the present invention to provide effective sunless tanning.

DETAILED DESCRIPTION OF THE INVENTION

Figure 1:
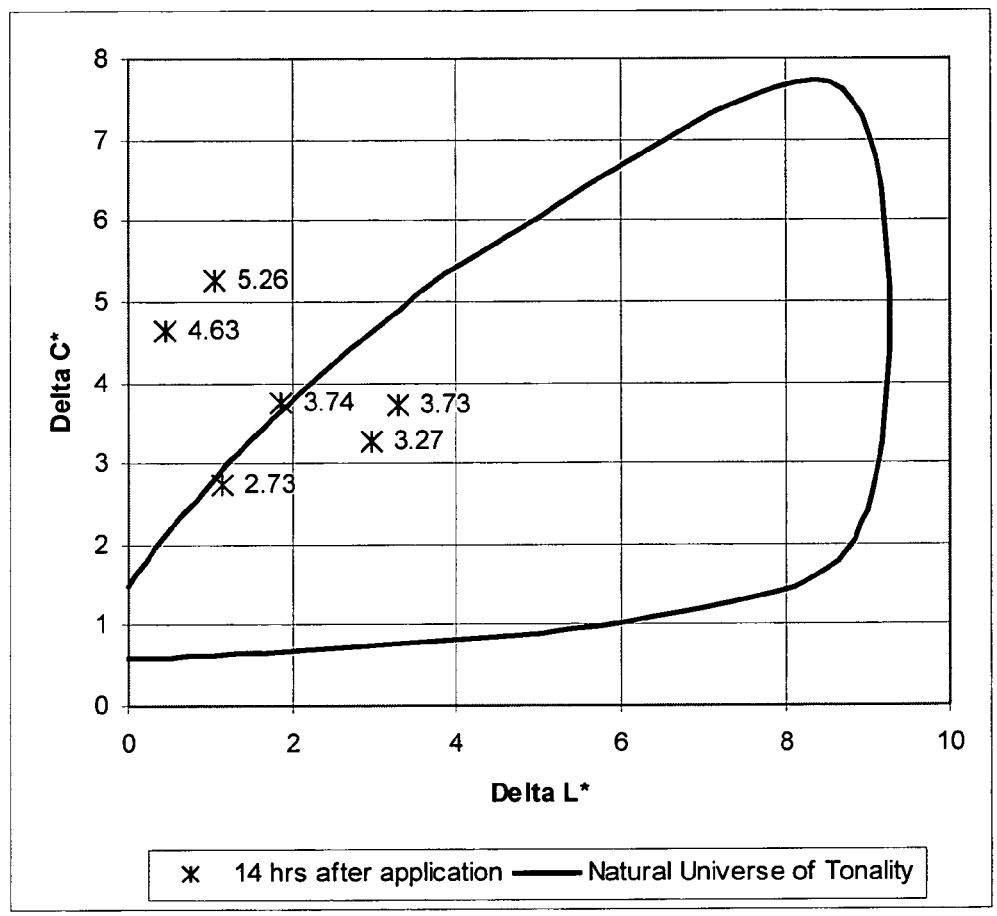
FIG. 1 is CIELAB plot of Delta C* versus Delta L*, which shows total chroma and lightness gradients of the skin treated with DHA-product alone or in conjunction with amphoacetates, according to an embodiment of the present invention.

The present invention provides a sunless tanning substrate having one or more sunless tanning enhancers, which adjust the rate of color development and/or adjust or customize the color developed on the skin. The substrate may be used prior to application, simultaneously with application, after application, or any combinations thereof, of one or more sunless tanning actives or agents to the skin.

Suitable substrates for use in the present invention include, but are not limited to, cloths, wipes, towels, towelettes, sponges, foams, battings, puffs, or any combinations thereof.

The substrates may be formed from fibrous sheet material, which may be woven, non-woven, or any combinations thereof.

Fibers from which the substrate may be formed can be natural, synthetic, or mixtures thereof. Suitable natural fibers from which to prepare the substrates herein include, for example, wood pulp, wool, silk, jute, hemp, cotton, linen, sisal, ramie, or any combinations thereof. Suitable synthetic fibers from which the substrates herein can be prepared include rayon, cellulose ester, polyvinyl derivatives, polyolefins, polyamides, acetate, acrylic, modacrylic fibers, polyester, polyurethane foam, or any combinations thereof. Suitable examples of some of these synthetic materials include acrylics such as acrilan, creslan, and the acrylonitrile-based fiber, orlon; cellulose ester fibers such as cellulose acetate, arnel, and acele; polyamides such as nylons (e.g., nylon 6, nylon 66, nylon 610, and the like); polyesters such as fortrel, kodel, and the polyethylene terephthalate fiber, dacron; polyolefins such as polypropylene, polyethylene; polyvinyl acetate fibers; polyurethane foams, or any combinations thereof. These and other suitable fibers, and the nonwoven materials prepared therefrom, are generally described in Riedel, "Nonwoven Bonding Methods and Materials," Nonwoven World (1987); The Encyclopedia Americana, vol. 11, pp. 147-153, and vol. 26, pp. 566-581 (1984); U.S. Pat. No. 4,891,227, to Thaman et al., issued Jan. 2, 1990; and U.S. Pat. No. 4,891,228, which are all incorporated by reference herein in their entirety.

For example, the nonwoven fibrous sheet materials may be meltblown, co-formed, air-laid, chemically-bonded, bonded-carded web materials, hydroentangled materials, and combinations thereof. The fibers may be directionally or randomly oriented fibers, bonded by friction, and/or cohesion and/or adhesion.

The fibers noted above may also be woven, knitted, tufted, or stitch-bonded to form a woven substrate for use in the present invention.

The sunless tanning substrate of the present invention includes one or more sunless tanning enhancers. The one or more enhancers may be included and/or disposed in and/or on the substrate in any manner and/or amount that achieves the desired result of adjusting the rate of color development and/or adjusting the color that develops on the skin. Preferably, the one or more tanning enhancers are formulated into an enhancing composition, that is then applied and/or loaded to any portion of the substrate in any suitable manner known in the art.

Suitable sunless tanning enhancers that may be used in the present invention include, but are not limited to, primary amines, oligomeric siloxane, amino acids, polyamines, amides, peptides, proteins, amphoglycinates, or any combinations thereof.

In an embodiment of the present invention, the one or more sunless tanning enhancers are one or more amphoglycinates represented by the formula:

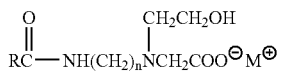

wherein the RC=O group represents the fatty acid residue derived from the specific oils or mixtures of oils used.

Thus, R can be a linear or branched $C_{10}$ to $C_{24}$ alkyl, any ranges therebetween or any mixtures thereof; wherein M is an alkali metal, such as, Li, Na, K and Cs; and n is an integer from 2 to 6.

In one embodiment according to the present invention, n is 2 and the one or more amphoglycinates are represented by the formula:

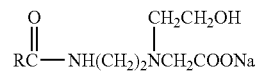

wherein R is a $C_{12}$ to $C_{22}$ alkyl. In another embodiment, R is a $C_{14}$ to $C_{20}$ alkyl. In yet another embodiment, R is a mixture of alkyls selected from linear and branched $C_{10}$ to $C_{24}$ alkyls and any ranges therebetween.

The one or more amphoglycinates can be sodium oliveamphoacetate, sodium sunflowerseed amphoacetate, sodium cocoabutter amphoacetate, sodium sesame amphoacetate, sodium sweetalmond amphoacetate, sodium caproamphoacetate, sodium capryloamphoacetate, sodium isostearoamphoacetate, sodium lauroamphoacetate, sodium myristoamphoacetate, sodium oleoamphoacetate, sodium palmamphoacetate, sodium peanutamphoacetate, sodium ricinoleoamphoacetate, sodium stearoamphoacetate, sodium tallowamphoacetate, sodium undecylenamphoacetate, sodium wheat germamphoacetate, sodium cocoyl glycinate (Amilite GCS-11, Ajinomoto), or any combinations thereof. These compounds are generally available from a variety of sources or can be prepared by methods known in the art.

Particular amphoglycinates that are commercially available and suitable for use in the present invention include:

Sodium Oliveamphoacetate (CAS No: 252750-70-1). Trade names: Kamapure Olive (Kama International Corp), Vamasoft olive (VaMa Farma Cosmetica, Italy);

Sodium Sunflowerseed Amphoacetate (CAS No: 252768-55-3). Trade name: Kamapure Sunflowers (Kama International Corp);

Sodium Cocoabutter Amphoacetate (CAS No: 252768-69-9). Trade name: Kamapure Cocoa (Kama International Corp);

Sodium Sesame Amphoacetate. Trade Name: Kamapure Sesame (Kama International Corp);

Sodium Sweetalmond Amphoacetate (CAS No 252768-53-1). Trade Name: Kamapure Sweet Almond (Kama International Corp); and Sodium Cocoyl Glycinate (Amilite GCS-11, Ajinomoto).

The technical or trade name vs. INCI names of some of the above are listed below:

| Technical/Trade Name | INCI Name |
|---|---|
| Caproamphoglycinate | Sodium caproamphoacetate |
| Caprylamphoglycinate | Sodium capryloamphoacetate |
| Cocoamphoglycinate | Sodium cocoamphoglycinate |
| Isostearoamphoglycinate | Sodium isostearoamphoacetate |
| Lauroamphoglycinate | Sodium lauroamphoacetate |
| Miristoamphoglycinate | Sodium myristoamphoacetate |
| Oleoamphoglycinate | Sodium oleoamphoacetate |
| Sodium palmamphoacetate | Sodium palmamphoacetate |
| Sodium peanutamphoacetate | Sodium peanutamphoacetate |
| Sodium ricinoleoamphoacetate | Sodium ricinoleoamphoacetate |
| Stearoamphoglycinate | Sodium stearoamphoacetate |
| Tallowamphoglycinate | Sodium tallowamphoacetate |
| Undecylenoamphoglycinate | Sodium undecylenamphoacetate |
| Disodium wheatgermamphoacetate | Disodium wheatgermamphoacetate |

While it is envisioned that the enhancing composition may include only the one or more sunless tanning enhancers (i.e. 100 wt. % of the total weight of the composition), the enhancing composition may further include one or more cosmetically acceptable vehicles. The one or more cosmetically acceptable vehicles may be present in an amount up to about 99.5 wt. %, based on the total weight of the enhancing composition.

In one embodiment, the one or more sunless tanning enhancers are present in an amount between about 0.1 wt. % to about 50 wt. %, based on the total weight of the enhancing composition. In another embodiment, the one or more sunless tanning enhancers are present in an amount between about 0.1 wt. % to about 30 wt. %, based on the total weight of the enhancing composition. In yet another embodiment, the one or more sunless tanning enhancers are present in an amount between about 1 wt. % to about 10 wt. %, based on the total weight of the enhancing composition. In still another embodiment, the one or more sunless tanning enhancers are present in an amount between about 1 wt. % to about 2 wt. %, based on the total weight of the enhancing composition.

In the context of the present invention, the term "cosmetically acceptable vehicle" or "suitable vehicle" refer to any vehicle for a drug, a cosmetic or a medicament that is suitable for use in direct, safe contact with human tissues. Examples include, but are not limited to, solutions, emulsions, dispersions, gels, or any combinations thereof.

The enhancing composition may further include one or more additional components, including, but not limited to, sugars, keto-sugars, surface-active agents, polymers, softening agents, moisturizers, water-proofing agents, vitamins, sweet orange citroflavonoids, hesperitine, ozone stressed yeast lysate, Saccharomyces cerevisiae ferment filtrate lysate, methylsulfonyl methane (MSM), also known as dimethyl sulfone and methyl sulfone, UV filters, skin penetration agents, or any combinations thereof.

Suitable UV filters that may be included in the enhancing composition include, but are not limited to, one or more of the following: dibenzoylmethane, oxybenzone, sulisobenzone, dioxybenzone, menthyl anthranilate, para aminobenzoic acid (PABA) ester, benzophenone-3, butyldibenzoylmethane (Parsol 1789), dimethyl cinnamate, octyl methoxycinnamate, DEA methoxycinnamate, octocrylene, drometrizole trisiloxane, octyl salicylate, homomenthyl salicylate, octyl dimethyl PABA, TEA salicylate, 4-methyl benzilidene camphor, 3-benzylidene camphor, benzylidene camphor sulfonic acid ester, octyl triazone, phenyl benzimidazole sulfonic acid ester, terephthalydiene dicamphor sulfonic acid ester, di-t-butyl hydroxybenzylidene camphor, ethyl PABA, butylmethoxy dibenzoylmethane (avobenzone), terephthalydiene methylene bis-benzotriazoyltetramethylbutyl-phenol, diethylhexyl-2,6-naphthalate, bis-ethylhexyloxyphenol methoxyphenol triazine, hydroxy methylphenyl benzotriazole, methylene bis-benzotriazoyltetramethylbutylphenol, bis-ethylhexyloxyphenol methoxyphenol triazine, hydroxybenzophenone, a benzotriazole, a dibenzoyl methane, an oxanilide, a hydroxy cinnamate, oil dispersible titanium dioxide, oil dispersible zinc oxide, a silicone-anchored sunscreen, para aminobenzoic acid (PABA), salicylic acid, TEA salicylate, benzylidene camphor sulfonic acid, phenyl benzimidazole sulfonic acid, terephthalydiene dicamphor sulfonic acid, hydroxy cinnamic acid, any derivatives thereof, or any combinations thereof.

Other suitable components that may be included in the enhancing composition of the present invention include, but are not limited to, antioxidants, such as, erythrobic acid, sodium metabisulfite, sodium sulfite, rosemary extract, tocopherol, derivative of tocopherol including tocotriene, carotene, carotenoid, lutein, lutein ester, phenolic antioxidant, bioflavonoid, plant extract, or any combinations thereof;

keratolytic agents, such as, salicylic acid, resorcinol, peroxide of an organic acid, or any combinations thereof;

anti-inflammatory agents, such as, steroidal and non-steroidal anti-inflammatory agents, plant extracts that have demonstrated anti-inflammatory activity, or any combinations thereof;

vitamins, such as, Vitamin K, Vitamin C, retinol (vitamin A), tocopherol, or any combinations thereof;

emollients, such as, cetearyl octanoate, octyl palmitate, butylene glycol, propylene glycol, glycerine, glyceryl monostearate, petrolatum, caprylic trigylceride, capric trigylceride, shae butter, silicone oil, or any combinations thereof;

humectants, such as, glycerin, propylene glycol, pentylene glycol, caprylyl glycol, hexylene glycol, butylene glycol, hyaluronic acid, one or more derivatives of hyaluronic acid, or any combinations thereof;

skin penetration enhancers, such as, ozone, SEPA, butylene glycol, cis-isomer of an unsaturated fatty acid, or any combinations thereof;

emulsifiers, such as, glyceryl stearate, cetearyl alcohol, cetyl alcohol and PEG-40 stearate, or any combinations thereof;

thickening agents, such as, xanthan gum, carbomer, clay, hydroxyethyl cellulose, or any combinations thereof;

preservatives, such as, an alkyl paraben, an alcohol, salts of benzoic acid, salts of sorbic acid, or any combinations thereof;

colorants, such as, synthetic and natural colorants including surface-treated or hydrophobically modified colorants, or any combinations thereof;

organic acids and their derivatives, such as citric acid, glycolic acid, glutamic acid, gluco delta lactone, or any combinations thereof;

chelating agents, such as, disodium EDTA;

pH adjusters, such as, an acid, a base, or a buffer, to adjust and maintain the pH to about 3 to about 7.5; and/or fragrances.

The one or more additional components set forth above may be present in an amount up to about 50 wt. %, based on the total weight of the enhancing composition. In one embodiment, the one or more additional components may be present in an amount about 1 wt. % to about 45 wt. %, based on the total weight of the enhancing composition. In another embodiment, the one or more additional components may be present in an amount about 5 wt. % to about 30 wt. %, based on the total weight of the enhancing composition.

The enhancing composition can be organic solvent based, water based, or it can be an emulsion.

In another embodiment of the present invention, the sunless tanning substrate includes an enhancing composition having one or more sunless tanning enhancers and one or more sunless tanning actives.

Suitable sunless tanning actives for use in the present invention include, but are not limited to, DHA, melanin, mahakanni (eclipta alba), erythrulose, or any combinations thereof. In one embodiment according to the present invention, the sunless tanning active is DHA.

The one or more sunless tanning actives may be present in the enhancing composition of the present invention in an amount about 0.5 wt. % to about 10 wt. % of the total weight of the enhancing composition. In one embodiment, the one or more sunless tanning actives may be present in the enhancing composition in an amount about 1 wt. % to about 7.5 wt. %. In another embodiment, the one or more sunless tanning actives may present in an amount about 1.5 wt. % to about 5 wt. %, of the total weight of the enhancing composition.

Similar to the above-described enhancing composition without one or more sunless tanning actives, the enhancing composition with both sunless tanning enhancer and sunless tanning active may include those additional components set forth above.

The present invention further provides a method of sunless tanning comprising the step of using the sunless tanning substrate of the present invention either prior to application, simultaneously with application, after application, or any combinations thereof, of one or more sunless tanning actives or agents to the skin. As a result of the method, the rate of color development and/or the color or color quality can be adjusted by the user.

By way of example, it is known that sunless tanning actives, such as DHA, react with amino acids, amines, polyamines, amides, peptides and proteins to produce a brownish color. However, it is the unexpected discovery of the present invention that the coloration of skin by one or more sunless tanning actives can be intensified and expedited by using the sunless tanning substrate having one or more sunless tanning enhancers before the application, after application, or simultaneously to application of the one or more sunless tanning actives to the skin.

In one embodiment of the present invention, the sunless tanning method includes the steps of (a) applying one or more sunless tanning actives to the skin; and (b) contacting the skin with a sunless tanning substrate having one or more sunless tanning enhancers.

In another embodiment of the present invention, the sunless tanning method includes the steps of (a) contacting the skin with a sunless tanning substrate having one or more sunless tanning enhancers; and (b) applying one or more sunless tanning actives to the skin.

In another embodiment of the present invention, the sunless tanning method includes the step of contacting the skin with a sunless tanning substrate having one or more sunless tanning enhancers and one or more sunless tanning actives.

It should be understood that the steps described in the above sunless tanning methods of the present invention can be repeated any number of times, in any sequence, as desired, until a satisfactory tanning color is obtained on the skin.

Depending on the concentration of the sunless tanning active and/or sunless tanning enhancer in the enhancing composition, color development typically starts within 4 to 6 minutes after the enhancing composition is applied to the skin. Therefore, the present method provides a uniform and natural looking sunless tan over all treated skin surfaces at a rate faster than known formulations.

The present invention also provides a sunless tanning kit. In one embodiment, the kit may include one or more sunless tanning substrates having one or more sunless tanning enhancers. This kit may be used by a consumer who separately provides a product having one or more sunless tanning actives.

In another embodiment of the present invention, the kit may include two separate components, namely a first component having one or more sunless tanning enhancers; and a second component having one or more sunless tanning actives. In one embodiment, the first component is one or more sunless tanning substrates in accordance with the present invention. It should be understood that the second component may also include one or more sunless tanning substrates, as described above, or may be any other suitable container/delivery device/dispenser for one or more sunless tanning actives.

In yet another embodiment of the present invention, the kit includes one or more sunless tanning substrates with a combination of one or more sunless tanning actives and one or more sunless tanning enhancers.

The above kits each allow a user to control or adjust the rate of color development on the skin and/or the color or color quality developed on the skin.

The Examples that follow are illustrative of the novelty of the present invention. The Examples should not be construed as being limiting in any manner whatsoever.

EXAMPLE 1

In vitro Tests

Color development in the model systems containing DHA and different amphoglycinates was evaluated after combining commercially available sunless tanner containing 5% of DHA (5 g) and different amphoglycinates (0.2 g) presented in Table 1.

Model systems were mixed until uniform and kept at 23° C. Times until the start of color development and color changes in the resulting systems were monitored.

Color readings were taken using the Minolta spectrophotometer with the following settings:

Reflectance Setting, SCI+SCE Specular Component, MAV (8 mm) Measurement Area, and 100% Full UV Setting.

The following CIELAB parameters were measured in order to evaluate the colors and their changes in the model systems:

Delta L* (lightness/darkness difference); Delta C* (total chroma difference); Delta a* that shows the red/green difference; Delta b* being the yellow/blue difference; Delta E* (total color difference) that integrates the differences between the L*, a*, and b* of the initial and developed color.

Data presented in Table 1 indicates that different amphoglycinates (amphoacetates) in conjunction with DHA can generate rapid color development (color development started in less than 5 min) and also different colors in model systems.

TABLE 1

Colors developed in the model systems containing DHA and different amphoglycinates (amphoacetates)

| | | Color Characteristics of the Model Systems (2 hrs after combining the ingredients) | | | | | |
|---|---|---|---|---|---|---|---|
| # | Model System | dL* (D65) | dC* (D65) | da* (D65) | db* (D65) | dE*ab (D65) | Start of Color Development |
| 1 | 5% DHA Cream + Sodium Sweetalmond Amphoacetate | 2.8 | 9.36 | −2.05 | 8.73 | 9.39 | 4'55" |
| 2 | 5% DHA Cream + Sodium Oliveampho-acetate | 5.44 | 11.8 | −1.77 | 10.94 | 12.34 | 4'59" |

TABLE 1-continued

Colors developed in the model systems containing DHA and different amphoglycinates (amphoacetates)

| # | Model System | Color Characteristics of the Model Systems (2 hrs after combining the ingredients) | | | | | Start of Color Development |
|---|---|---|---|---|---|---|---|
| | | dL* (D65) | dC* (D65) | da* (D65) | db* (D65) | dE*ab (D65) | |
| 3 | 5% DHA Cream + Sodium Sunflowerseed Amphoacetate | 10.21 | 18.29 | −3.24 | 17.63 | 5.02 | 4'50" |
| 4 | 5% DHA Cream + Sodium Sesame Amphoacetate | 13.44 | 13.01 | −2.02 | 12.92 | 3.24 | 4'30" |

The differences in Delta L* values (lightness/darkness), Delta C* (total chroma) as well as Delta a* (red/green color coordinate) and Delta b* (yellow/blue) were very pronounced. The total color differences (Delta E*) attributed to different amphoacetates varied in the range of 3 to 12.

Sodium oliveamphoacetate generated the most dramatic total color difference (Delta E* of 12.34), followed by Sodium sweetalmond amphoacetate (with Delta E* of 9.39). These findings indicate that the nature of fatty acid in the amphoacetate structure can influence color development and color characteristics in the model systems containing DHA and specific amphoacetate.

EXAMPLE 2

In vivo Tests

Skin color developed after application of the commercially available sunless tanning product, a mousse containing 5% DHA (control), was compared with skin color developed after application of control followed by the application of 25% aqueous solutions of selected amphoglycinates (amphoacetates) presented in Table 2.

Panelists with Type 1-2 skin were employed. Their forearms were gently exfoliated, rinsed and dried. Initial readings (base readings) of the designated areas on each forearm were taken by Minolta spectrophotometer with the following settings:

Reflectance Setting, SCI+SCE Specular Component, MAV (8 mm) Measurement Area, and 100% Full UV.

The following CIELAB parameters were measured in order to evaluate the skin colors and their changes: Delta L* (lightness/darkness difference); Delta C* (chroma difference); Delta a* that shows the red/green difference; Delta b* being the yellow/blue difference; Delta E* (total color difference) that integrates the differences between the L*, a*, and b* of the initial and developed color.

A 4 mg/cm² dose of the sunless tanner was applied to the forearms and gently rubbed into the skin using a finger-cot.

After 10 min of the application, a 2 mg/cm² of the solution of the tested amphoglycinates were applied on the designated areas (12 sq.cm) and gently rubbed into the skin. Color measurements were taken again using a Minolta spectrophotometer 14 hrs after application.

The "natural universe" of tan and tonality data presented on the graphs (FIGS. 1 and 2) as solid black lines was obtained from a study conducted by Estee Lauder (Muizzuddin N, Marenus K, Maes D., Tonality of suntan vs. sunless tanning with dihydroxyacetone). Skin Research and Technology 2000; 6: 199-204). "Natural universe" of color was determined by the color achieved from a natural suntan.

Figure 2:
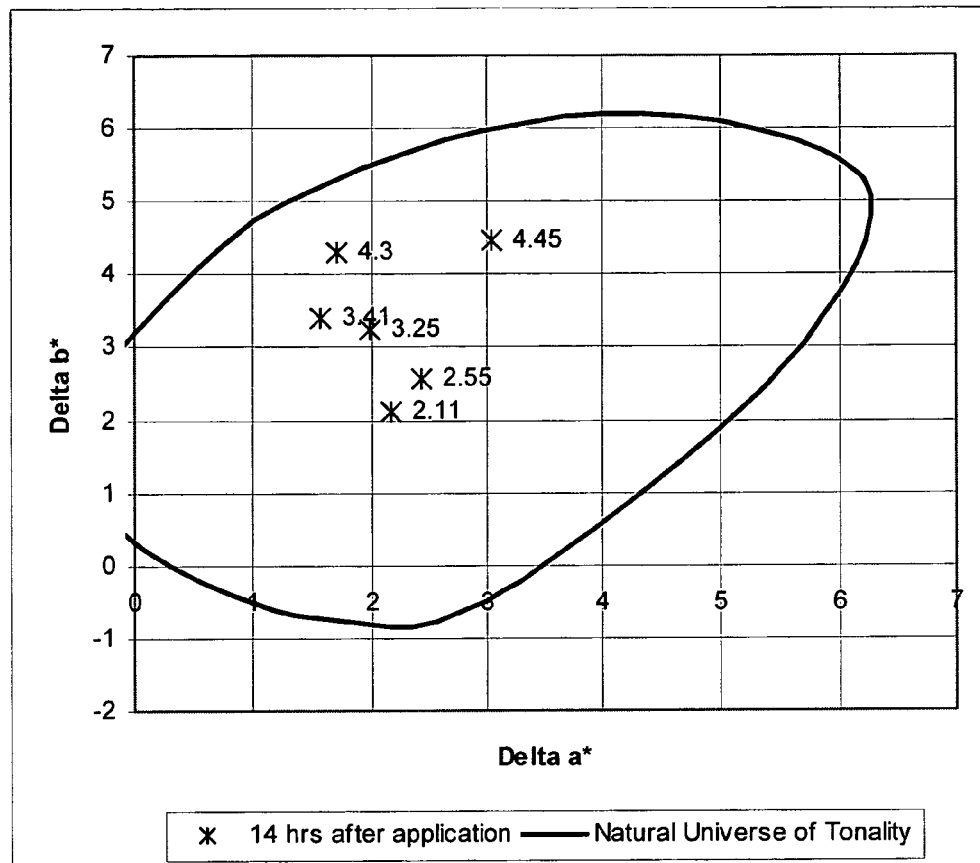
FIG. 2 is CIELAB plot of Delta b* versus Delta a*, which shows the color characteristics of the skin treated with DHA-product alone or in conjunction with amphoacetates, according to an embodiment of the present invention.

Referring to Table 2, FIG. 1 and FIG. 2, it can be seen that different amphoglycinates in conjunction with DHA can generate various skin tones that differ from the color generated by DHA containing formulation alone (control).

In the Figures the CIELAB color space model has been utilized. Widely accepted CIELAB color space is used within the cosmetic industry to evaluate skin colors. The CIELAB color space is a three dimensional space, where every color can be located. The location of any color in the space is determined by its color coordinates: L*, a*, and b*, where:

L*—the lightness/darkness coordinate;

a*—the red/green coordinate, with +a* indicating red and −a* indicating green;

b*—the yellow/blue coordinate, with +b* indicating yellow, and −b* indicating blue.

CIELAB total color difference is the distance between the color locations, which can be expressed as Delta E, where:

$$\text{Delta } E^* = (\text{Delta } L^{*2} + \text{Delta } a^{*2} + \text{Delta } b^{*2})^{1/2}.$$

Delta E* is a total color difference, which integrates the differences between the L*, a*, and b* of the initial skin (sample) color and skin (sample) color that was developed. C* is the chroma coordinate: $C^* = [(a^*)^2 + (b^*)^2]^{1/2}$, and Delta C* is the total chroma difference between the initial and developed color. Delta L* indicates the lightness/darkness difference.

Positive value (+) of Delta L* means that developed color is lighter than initial and negative (−) Delta L* means that developed color is darker than initial. Delta a* shows the red/green difference. Positive value (+) of delta a* indicates that developed color is redder (or less green) than initial and negative (−) delta a* value means that developed color is less red (or greener) than initial. Delta b* describes the yellow/blue difference. Positive value (+) of Delta b* indicates that developed color is yellower (or less blue) than initial and negative (−) Delta b* means that developed color is less yellow (or bluer) than initial.

FIG. 1 is CIELAB plot of Delta C* versus Delta L*. It shows total chroma and lightness changes of the skin treated with DHA-product alone or in conjunction with amphoacetates.

"Natural universe" of color determined by the skin color achieved from a natural suntan (or actual sun exposure) is used in the present invention as the reference.

Referring to FIG. 1, it can be seen that the tan achieved with the use of sunless tanner in conjunction with sodium sweetalmond amphoacetate (dL* 2.95; dC* 3.27), sodium cocoyl glycinate (dL* 1.86; dC* 3.74), sodium sunflowerseed amphoacetate (dL* 3.28; dC* 3.73), and sodium sesame amphoacetate (dL* 1.14; dC* 2.73), are different but did fall within this "natural universe" of color characteristics (dL* and dC*) developed after actual sun exposure and presented on the FIG. 1 as solid black line.

Interestingly, skin tone generated by the control (dL* 0.44; dC* 4.63) was outside of "natural universe" of color.

Referring to FIG. 2, it can be seen that it is CIELAB plot of Delta b* versus Delta a*. It shows the color characteristics of the skin treated with DHA-product alone or in conjunction with amphoacetates. Delta b* and Delta a* values indicate that the tan achieved with the use of sunless tanner in conjunction with sodium sweetalmond amphoacetate (db* 2.55; da* 2.44), sodium cocoyl glycinate (db* 3.41; da* 1.56), sodium sunflowerseed amphoacetate (db* 3.25; da* 1.98), sodium sesame amphoacetate (db* 2.11; da* 2.17) and sodium oliveamphoacetate (db* 4.45; da* 3.05) are different from the color changes induced by control (db* 4.3; da* 1.71) and did fall within this "natural universe" of color characteristics (db* and da*) developed on skin after actual sun exposure and presented on the FIG. 2 as solid black line.

Table 2 shows the differences in skin tone developed after application of the sunless tanner alone and in conjunction with amphoacetates.

TABLE 2

Differences in skin tone

| # | Data Name | dL* (D65) | dC* (D65) | da* (D65) | db* (D65) | dE*ab (D65) |
|---|---|---|---|---|---|---|
| 1 | 5% DHA Mousse (Control) | 0.44 | 4.63 | 1.71 | 4.3 | 4.65 |
| 2 | 5% DHA Mousse + Sodium Sweetalmond Amphoacetate | 2.95 | 3.27 | 2.44 | 2.55 | 4.6 |
| 3 | 5% DHA Mousse + Sodium Cocoyl Glycinate | 1.86 | 3.74 | 1.56 | 3.41 | 4.18 |
| 4 | 5% DHA Mousse + Sodium Oliveamphoacetate | 1.04 | 5.26 | 3.05 | 4.45 | 5.49 |
| 5 | 5% DHA Mousse + Sodium Sunflowerseed Amphoacetate | 3.28 | 3.73 | 1.98 | 3.25 | 5.02 |
| 6 | 5% DHA Mousse + Sodium Sesame Amphoacetate | 1.14 | 2.73 | 2.17 | 2.11 | 3.24 |

The findings described above indicate that the nature of fatty acid in the amphoacetate structure can influence skin color development and skin color characteristics when products containing a sunless tanning active, such as DHA, are used in conjunction with specific amphoacetate, which is an unexpected and useful discovery.

Various DHA-containing and amphoglycinate-containing types of formulas can be utilized in sunless tanning systems in different delivery system and packages, such as, creams, lotions, solutions, sprays/wipes, dual-chamber tubes and aerosols. A composition with Amphoglycinate that can be used as the part of a sunless tanning system comprises two cosmetic formulations, one containing DHA and one containing one or more amphoglycinates that can be mixed at the time of use or also can be applied successively to the skin, as a leave on or a wash-off formulation, one after the other.

EXAMPLE 3

A composition with Amphoglycinate and no sunless tanning active component is exemplified below.

Composition with Amphoacetate (Amphoglycinate):

| Ingredient | Wt % |
|---|---|
| Amphoacetate (Amphoglycinate) | 0.1-30 |
| Glycerin | 1-20 |
| Cocamidopropyl Betaine (30%) | 0-5 |

Composition with Amphoacetate (Amphoglycinate):

| Ingredient | Wt % |
|---|---|
| Lauric Acid | 0-1 |
| Myristic Acid | 0-1 |
| Glycol Distearate | 0-5 |
| Behenyl Alcohol | 0-5 |
| Polyquaternium-39 (10%) | 0-1 |
| Citric Acid | 0-1 |
| Pentylene Glycol | 0-5 |
| Water | to 100 |

The amphoglycinate can be one or more of the following: sodium oliveamphoacetate, sodium sunflowerseed amphoacetate, sodium cocoabutter amphoacetate, sodium sesame amphoacetate, sodium sweetalmond amphoacetate, sodium caproamphoacetate, sodium capryloamphoacetate, sodium isostearoamphoacetate, sodium lauroamphoacetate, sodium myristoamphoacetate, sodium oleoamphoacetate, sodium palmamphoacetate, sodium peanutamphoacetate, sodium ricinoleoamphoacetate, sodium stearoamphoacetate, sodium tallowamphoacetate, sodium undecylenamphoacetate, sodium wheat germamphoacetate, sodium cocoyl glycinate, or any mixtures thereof.

Advantageously, a composition, such as that exemplified in Example 3, may be provided as a stand-alone sunless tanning enhancer product or may be provided as an enhancing component of a sunless tanning kit. The enhancing composition could be applied prior to, simultaneously with, or after application of one or more sunless tanning actives to the skin.

EXAMPLE 4

A one-component formulation was prepared as follows:

At room temperature DHA was added to the water, mixed until dissolved. Hydroxyethylacrylate/sodium (and) Acryloyidimethyltaurate Copolymer (and) Squalane (and) Polysorbate-60 were added under vigorous agitation and continued mixing for 10-15 min. PPG-11 stearyl ether was then added slowly followed by amphoglycinate, preservative and fragrance.

ONE-COMPONENT FORMULATION
This composition is formed immediately after mixing all of the ingredients at once for immediate use.

| Ingredient: | Wt %: |
|---|---|
| Water | Q.s. to 100 |
| Dihydroacetone | 1-10 |
| Hydroxyethylacrylate/sodium (and) Acryloyldimethyltaurate copolymer (and) Squalane (and) Polysorbate-60 | 2-3 |
| PPG-11 Stearyl Ether | 4-6 |
| Amphoglycinate | 1-2 |
| Preservative[a] | 0.5-1 |
| Fragrance | 0-0.2 |

Preservative[a]: Phenoxyethanol (and) Methylparaben (and) Ethylparaben (and) Propylparaben (and), Butylparaben (and) Isobutylparaben

EXAMPLE 5

A two-component formulation was prepared as follows:
Components of Phase A and B were combined in two separate vessels, heated to 70-75° C. with mixing until uniform and combined at 70-75° C. with homogenization. The combined phases were cooled to 40° C. with mixing. Phase C was added at 40° C. with mixing until uniform.

This composition is formed as two component formulations:

COMPONENT A, which is the first component of the two-component formulation and COMPONENT B, which is the second component of the two-component formulation.

COMPONENT A and COMPONENT B are mixed just prior to use to produce a final composition having all of the necessary ingredients for immediate use.

Thereafter, the final composition is applied immediately after mixing.

| COMPONENT A | |
|---|---|
| | Wt %: |
| Phase A: | |
| Glyceryl Stearate (and) PEG-100 Stearate | 3-4 |
| Caprylic Capric Triglycerides | 3.5-4.5 |
| C12-15 Alkyl Benzoate | 2-3 |
| Cetyl Alcohol | 2-3 |
| PEG-7 Glyceryl Cocoate | 0.3-0.5 |
| Dimethicone | 0.3-1 |
| Stearic Acid | 0.6-1 |
| Petrolatum | 0-1.2 |
| Stearyl Alcohol | 1.9-2.1 |
| Steareth-2 | 0.2-0.3 |
| Steareth-20 | 0.3-0.4 |
| Tocopherol | 0.1-0.5 |
| Preservative$^a$ | 0.5-1 |
| Phase B | |
| Water | Qs to 100 |
| Aloe Vera Juice | 0.1-1 |
| Disodium EDTA | 0.05-0.1 |
| Phase C: | |
| Water | 10-12 |
| Propylene Glycol | 3-5 |
| Dihydroacetone | 1-10 |
| Fragrance | 0-0.3 |
| Citric Acid | Qs to a pH of 3.5-4.5 |

Preservative$^a$: Phenoxyethanol (and) Methylparaben (and) Ethylparaben (and) Propylparaben (and), Butylparaben (and) Isobutylparaben

| COMPONENT B | |
|---|---|
| | Wt %: |
| Phase A: | |
| Glyceryl Stearate (and) PEG-100 Stearate | 3-4 |
| Caprylic Capric Triglycerides | 3.5-4.5 |
| C12-15 Alkyl Benzoate | 2-3 |
| Cetyl Alcohol | 2-3 |
| PEG-7 Glyceryl Cocoate | 0.3-0.5 |
| Dimethicone | 0.3-1 |
| Stearic Acid | 0.6-1 |
| Petrolatum | 0-1.2 |
| Stearyl Alcohol | 1.9-2.1 |
| Steareth-2 | 0.2-0.3 |
| Steareth-20 | 0.3-0.4 |
| Tocopherol | 0.1-0.5 |
| Preservative$^a$ | 0.5-1 |
| Phase B | |
| Water | Qs to 100 |
| Aloe Vera Juice | 0.1-1 |
| Disodium EDTA | 0.05-0.1 |

| COMPONENT B (continued) | |
|---|---|
| | Wt %: |
| Phase C: | |
| Water | 10-12 |
| Propylene Glycol | 3-5 |
| Amphoglycinate | 1-10 |
| Fragrance | 0-0.3 |
| Citric Acid | Qs to a pH of 3.5-4.5 |

Preservative$^a$: Phenoxyethanol(and) Methylparaben(and) Ethylparaben(and) Propylparaben(and) Butylparaben (and) Isobutylparaben.

Advantageously, a two-component product, such as that exemplified above in Example 5, may be provided to a consumer in a sunless tanning kit, which includes one or more sunless tanning substrates with Component A and separately one or more sunless tanning substrates with Component B. Component A and Component B could then be applied to the skin by a consumer in any order, frequency and/or amount to achieve the desired sunless tan.

It should be understood that the formulations set forth in the examples may be dispersed and/or loaded to one or more sunless tanning substrates in accordance with the present invention, as set forth herein.

In one embodiment of the present invention, the enhancing composition may be loaded to a substrate in an amount between about 0.5 grams to about 30 grams per substrate. The actual amount loaded to a substrate may depend, in part, on the type of substrate used, the size of the substrate used, and/or the surface area of the skin to be treated.

It should also be understood that the foregoing description is only illustrative of the present invention. Various alternatives and modifications can be devised by those skilled in the art without departing from the scope of the present invention and claims set forth herein.

We claim:

1. A sunless tanning substrate consisting of:
    said substrate; and
    an enhancing composition, said enhancing composition consisting of:
        one or more sunless tanning enhancers present in an amount of about 0.1 wt. % to about 50 wt. %, based on a total weight of said enhancing composition;
        one or more sunless tanning actives present in an amount of about 0.5 wt. % to about 10 wt. %, based on a total weight of said enhancing composition; and
        water, an organic solvent, or a combination of the two,
    wherein said one or more sunless tanning enhancers are one or more amphoglycinates selected from the group consisting of sodium oliveamphoacetate, sodium sunflowerseed amphoacetate, sodium cocoabutter amphoacetate, sodium sesame amphoacetate, sodium sweetalmond amphoacetate, and sodium cocoyl glycinate.

2. The sunless tanning substrate of claim 1, wherein said substrate is selected from the group consisting of cloths, wipes, towels, towelettes, sponges, foams, battings, puffs, and any combinations thereof.

3. The sunless tanning substrate of claim 1, wherein said one or more sunless tanning enhancers are present in an amount of about 1 wt. % to about 10 wt. %, based on a total weight of said enhancing composition.

4. The sunless tanning substrate of claim 1, wherein said one or more sunless tanning actives are selected from the group consisting of DHA, melanin, mahakanni (eclipta alba), erythrulose, and any combinations thereof.

5. The sunless tanning substrate of claim 1, wherein said one or more sunless tanning actives is present in said enhancing composition in an amount about 1 wt. % to about 7.5 wt. % of the total weight of said enhancing composition.

6. The sunless tanning substrate of claim 1, wherein said one or more sunless tanning actives is present in said enhancing composition in an amount about 1.5 wt. % to about 5 wt. % of the total weight of said enhancing composition.

7. A method of sunless tanning comprising the steps of:
providing a sunless tanning substrate consisting of a substrate and an enhancing composition, said enhancing composition consisting of:
one or more sunless tanning enhancers selected from the group consisting of sodium oliveamphoacetate, sodium sunflowerseed amphoacetate, sodium cocoabutter amphoacetate, sodium sesame amphoacetate, sodium sweetalmond amphoacetate, and sodium cocoyl glycinate;
water, an organic solvent, or a combination thereof; and
contacting an area of skin with said sunless tanning substrate either prior to application, simultaneously with application, after application, or any combinations thereof, of one or more sunless tanning actives to said skin.

8. The method of claim 7, wherein said area of skin is contacted with said sunless tanning substrate after applying said one or more sunless tanning actives to said skin.

9. The method of claim 7, wherein said area of skin is contacted with said sunless tanning substrate prior to applying said one or more sunless tanning actives to said skin.

10. The method of claim 7, wherein said area of skin is contacted with said sunless tanning substrate simultaneously with said application of said one or more sunless tanning actives to said skin.

11. The method of claim 10, wherein said one or more sunless tanning actives are included in said enhancing composition.

12. The method of claim 10, wherein said one or more sunless tanning actives are applied to said skin from a separate application means than said sunless tanning substrate.

13. The method of claim 7, wherein said method steps are repeated any number of times and/or in any sequence until a desired tanning color is obtained on said skin.

14. The method of claim 7, wherein a color development begins about 4 minutes to about 6 minutes after said contacting step.

15. The method of claim 7, wherein said substrate is selected from the group consisting of cloths, wipes, towels, towelettes, sponges, foams, battings, and puffs.

16. The method of claim 11, wherein said one or more sunless tanning actives are selected from the group consisting of DHA, melanin, mahakanni (eclipta alba), erythrulose, and any combinations thereof.

17. The method of claim 11, wherein said one or more sunless tanning actives is present in said enhancing composition in an amount about 0.5 wt.% to about 10 wt. % of the total weight of said enhancing composition.

18. A sunless tanning kit comprising:
a first component consisting of:
one or more sunless tanning enhancers, wherein said one or more sunless tanning enhancers are one or more amphoglycinates selected from the group consisting of sodium oliveamphoacetate, sodium sunflowerseed amphoacetate, sodium cocoabutter amphoacetate, sodium sesame amphoacetate, sodium sweetalmond amphoacetate, and sodium cocoyl glycinate;
water, an organic solvent, or a combination thereof; and
a second component comprising one or more sunless tanning actives.

19. The kit of claim 18, wherein said first component is a sunless tanning substrate.

20. The kit of claim 19, wherein said substrate is selected from the group consisting of cloths, wipes, towels, towelettes, sponges, foams, battings, puffs, and any combinations thereof.

21. The kit of claim 18, wherein said one or more sunless tanning actives are selected from the group consisting of DHA, melanin, mahakanni (eclipta alba), erythrulose, and any combinations thereof.

22. A sunless tanning kit consisting of one or more sunless tanning substrates, said one or more substrates consisting of one or more sunless tanning actives and one or more sunless tanning enhancers, wherein said one or more sunless tanning enhancers are one or more amphoglycinates selected from the group consisting of: sodium oliveamphoacetate, sodium sunflowerseed amphoacetate, sodium cocoabutter amphoacetate, sodium sesame amphoacetate, sodium sweetalmond amphoacetate, and sodium cocoyl glycinate.

23. The kit of claim 22, wherein said one or more substrates is selected from the group consisting of cloths, wipes, towels, towelettes, sponges, foams, battings, puffs, and any combinations thereof.

24. The kit of claim 22, wherein said one or more sunless tanning actives are selected from the group consisting of DHA, melanin, mahakanni (eclipta alba), erythrulose, and any combinations thereof.

25. The sunless tanning substrate of claim 8, wherein said one or more sunless tanning enhancers are present in an amount of about 1 wt. % to about 2 wt. %, based on a total weight of said enhancing composition.

* * * * *